United States Patent [19]
Ruiz

[11] Patent Number: 4,573,476
[45] Date of Patent: Mar. 4, 1986

[54] ANGIOGRAPHIC CATHETER

[76] Inventor: Oscar F. Ruiz, 3655 Bay Homes Dr., Coconut Grove, Fla. 33133

[21] Appl. No.: 551,561

[22] Filed: Nov. 14, 1983

[51] Int. Cl.⁴ .............................................. A61M 25/00
[52] U.S. Cl. ..................................... 128/658; 604/280
[58] Field of Search ................................ 604/280–281; 128/656–658

[56] References Cited
U.S. PATENT DOCUMENTS

| | | | |
|---|---|---|---|
| 3,938,501 | 2/1976 | Erikson | 128/658 |
| 4,169,464 | 10/1979 | Obrez | 128/658 X |
| 4,279,252 | 7/1981 | Martin | 128/658 |
| 4,385,635 | 5/1983 | Ruiz | 128/658 |

OTHER PUBLICATIONS

Cordis Phamphlet-1973 "Cordis Ducor" Item 521-732 p. 16.

*Primary Examiner*—Dalton L. Truluck
*Attorney, Agent, or Firm*—Eugene F. Malin

[57] ABSTRACT

An angiographic catheter for delivery of radio opaque contrast media having intra-vacularly means for reducing the pressure of the radio opaque contrast media through the terminal end while maintaining sufficient volume for avoiding dilution. This improved catheter decreases the shock and damage to the vessel wall and allows sufficient contrast media to reach the vessels thereby avoiding the problems of dilution.

5 Claims, 2 Drawing Figures

ANGIOGRAPHIC CATHETER

BACKGROUND OF THE INVENTION

Angiographic catheters have been used in cardiographic studies and digital subtraction angiographic studies. Intravenous digital subtraction angiography is presently being used to image cerebral, renal, peripheral, pulmonary and cardiographic arterial systems. The radio opaque contrast media is induced through use of a pigtail catheter and a bolus injection of contrast material. The pigtail catheters have historically been used for cardiac angiography. The pigtail catheter was developed by Melvin P. Judkins. Current pigtail catheters on the market include Cordis, Cook, U.S.C.I., Mallinckrodt, U.M.I. and Vertex. The pigtail catheter includes a relatively straight elongated member with a plurality of holes in the linear portion. The terminal end of the catheter has a decreased diameter, which may include a decreased interior lumen or a decreased exterior diameter. The decreased lumen portion is pigtail shaped, that is coiled on itself.

The pigtail catheter was designed to allow minimum flow out of the end-opening while delivering a large proportion of contrast material through the side opening.

SUMMARY OF THE INVENTION

It is an object of this invention to provide an improved catheter for angiographic studies and digital subtraction angiographic (DSA) studies which will dispense the radio opaque contrast material by dispensing approximately 70% of the contrast material prior to exiting the terminal end of the catheter tip.

It is a further object of this invention to decrease the likelihood of clots forming at the aperture sites by limiting the lateral apertures to two in number.

It is a further object of this invention to place the side apertures on the radius of the curve rather than on the straight part of the catheter or very proximal to the tip as in other catheters.

It is a further object of this invention to reduce the shock from exiting contrast material to the vessel wall by positioning the apertures in an arcuate or aquiline intermediate zone allowing the contrast material to exit at an angle of greater than 90°.

DESCRIPTION OF THE PREFERRED EMBODIMENT

Figure 1:
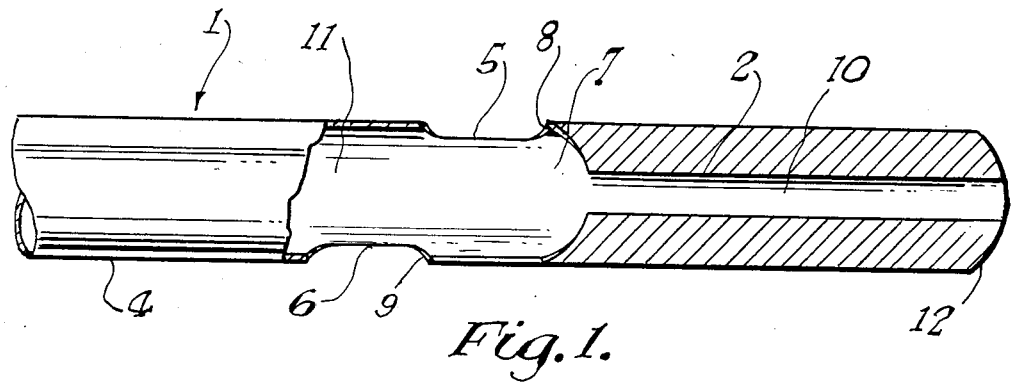
FIG. 1 is a side view of the terminal and of the angiographic catheter.
Figure 2:
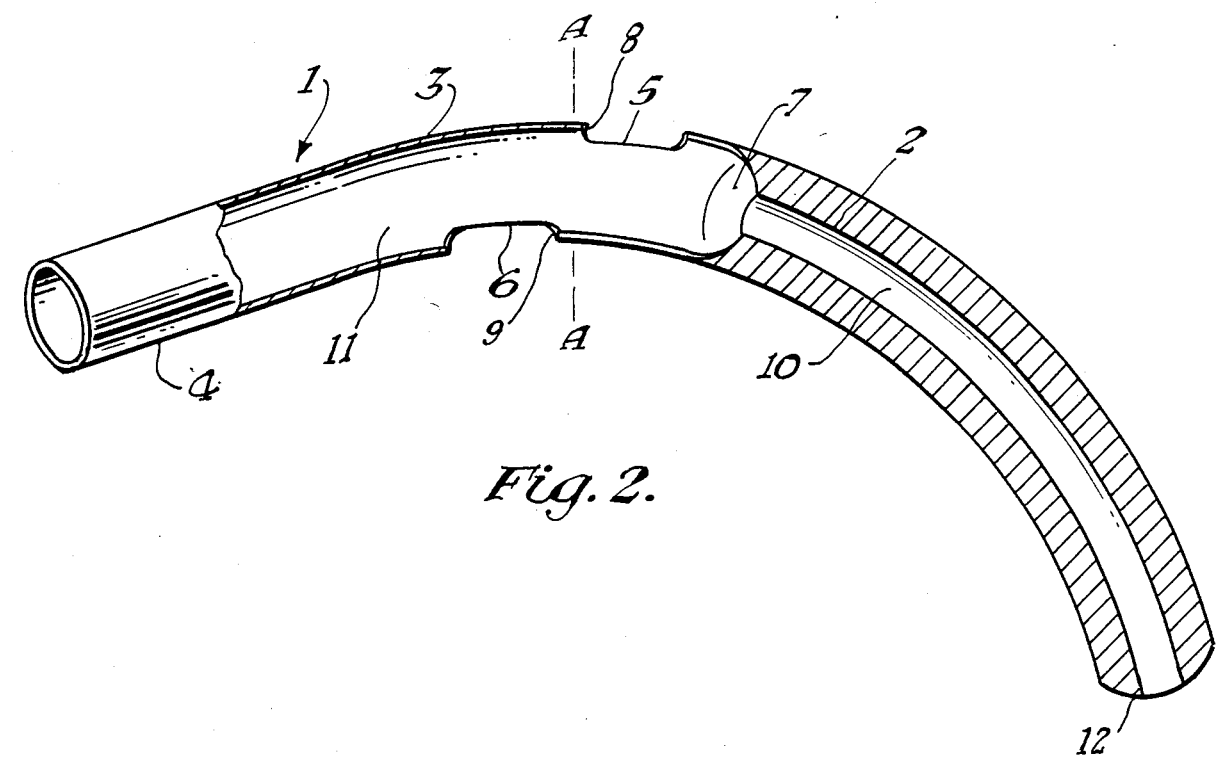
FIG. 2 is a cross section of the terminal end of the catheter.

Referring to FIGS. 1 and 2, the improved catheter 1, includes a soft flexible, pliable leading tip zone 2, as disclosed in U.S. Pat. No. 4,385,635, herein incorporated by reference, an intermediate member 3 of arcuate or aquiline shape having a tapered distal end 7 and an elongated member 4. Intermediate member 3 includes a first aperture 5 closely adjacent to tapered portion 7 and a second aperture 6 opposite and above the first aperture, both apertures being preferably, ellipsoidal in shape. The contrast material is introduced into the vascular system as a bolus injection under pressure. The ellipsoidal shape of the first and second apertures is preferable as they allow egress of the contrast material at an angle greater than 90° thus reducing the likelihood of the contrast material directly impinging onto the vessel wall. The first (5) and second (6) apertures are so shaped and of a size to discharge at least about 70% of the contrast material injected to flow through them in the improved catheter. The remaining contrast material exits the terminal end 12 of the tip zone 2. The first and second apertures of the catheter are positioned perpendicular to the longitudinal axis of the intermediate member 3. The first aperture 5 is positioned closely adjacent to the tapered portion 7 of the intermediate member 3 with its proximal end 8 closely adjacent to the A—A axis. The second aperture 6 is positioned opposite the first aperture 5 with its distal end 9 closely adjacent to the A—A axis.

The tapered portion 7 permits utilization of a smaller lumen 10 as compared to the larger lumen 11 of the intermediate portion 3 and the elongated member 4. The construction of the soft tip end is disclosed in U.S. Pat. No. 4,385,635.

The instant invention has been shown and described herein in what is considered to be the most practical and preferred embodiment.

What I claim is:

1. An improved angiographic catheter for injection of radio opaque contrast material intra vascularly comprising:

an elongated horizontal member;
    an intermediate member said elongated horizontal member and said intermediate member including a lumen portion;
    a tip zone member, including a smaller lumen portion, said smaller lumen having a constant diameter and opening out through the tip end, said members being functionally integral;
    said intermediate member positioned between said elongated horizontal member and said tip zone member;
    said intermediate member including at least a first and a second aperture;
    said first aperture positioned between said tip zone member and said intermediate member;
    said second aperture positioned between said first aperture and said elongated horizontal member;
    said aperture being of a size to permit approximately 70% of the contrast material to flow therethrough while the remaining 30% exits through the small lumen tip end, said side flow reducing shock to the blood vessel wall during angiographic procedures,
    said intermediate member being curved from said elongated horizontal member at an angle of less than 90° and
    said intermediate member being curved from said elongated horizontal member at an angle of less than 90° and having its free end space a short distance from the longitudinal axis of said elongated horizontal member.

2. An improved angiographic catheter as set forth in claim 1, wherein:

said intermediate catheter member is aquiline-shaped.

3. An improved catheter as set forth in claim 2, wherein:

said intermediate member includes a tapered portion at the terminal end thereof;
    said first aperture being located closely adjacent to said terminal end of said intermediate member;

said second aperture disposed or located opposite and staggered relative to said first aperture.

4. An improved angiographic catheter as set forth in claim 3, wherein:
said first aperture being ellipsoidal-shaped;
said second aperture being ellipsoidal-shaped.

5. An improved angiographic catheter as set forth in claim 3, wherein:
said first and second apertures are ellipsoidal-shaped;
said ellipsoidal-shape allowing egress of the contrast material at an angle greater than 90°.

* * * * *